United States Patent
Gebert et al.

(10) Patent No.: US 10,653,383 B2
(45) Date of Patent: May 19, 2020

(54) COMPUTED TOMOGRAPHY DEVICE AND METHOD FOR DETERMINING AN OPERATING STATE OF SLIDING CONTACTS IN A COMPUTED TOMOGRAPHY DEVICE

(71) Applicant: Siemens Healthcare GmbH, Erlangen (DE)

(72) Inventors: Bernhard Gebert, Hagenau (DE); Markus Krauss, Waischenfeld (DE)

(73) Assignee: SIEMENS HEALTHCARE GMBJ, Erlangen (DE)

( * ) Notice: Subject to any disclaimer, the term of this patent is extended or adjusted under 35 U.S.C. 154(b) by 0 days.

(21) Appl. No.: 16/433,322

(22) Filed: Jun. 6, 2019

(65) Prior Publication Data
US 2019/0380673 A1 Dec. 19, 2019

(30) Foreign Application Priority Data

Jun. 19, 2018 (EP) .................................... 18178537

(51) Int. Cl.
| | |
|---|---|
| A61B 6/03 | (2006.01) |
| G01R 27/26 | (2006.01) |
| G01R 27/28 | (2006.01) |
| H01R 39/26 | (2006.01) |
| A61B 6/00 | (2006.01) |

(52) U.S. Cl.
CPC .................. A61B 6/58 (2013.01); A61B 6/56 (2013.01); G01R 27/2611 (2013.01); G01R 27/28 (2013.01); H01R 39/26 (2013.01)

(58) Field of Classification Search
CPC ........... A61B 6/032; A61B 6/035; A61B 6/56; A61B 6/58; A61B 6/586; G01R 27/2611; G01R 27/28; H01R 39/26
See application file for complete search history.

(56) References Cited

U.S. PATENT DOCUMENTS

| | | |
|---|---|---|
| 5,402,461 A | 3/1995 | Kudo |
| 6,424,159 B1 | 7/2002 | Jansen et al. |

FOREIGN PATENT DOCUMENTS

| | | |
|---|---|---|
| CN | 104545979 A | 4/2015 |
| DE | 10120088 A1 | 10/2001 |
| DE | 102006011968 A1 | 9/2007 |
| JP | H07265291 A | 10/1995 |

OTHER PUBLICATIONS

NPL: Extented European Search Report for EP Application Patent No. 18178537, dated Dec. 14, 2018 and English translation herewith.

*Primary Examiner* — Mark R Gaworecki
(74) *Attorney, Agent, or Firm* — Harness, Dickey & Pierce, P.L.C.

(57) ABSTRACT

A computed tomography device includes a slipring for rotational transmission and a feed line. The slipring is arranged to be rotatable relative to the feed line. Two sliding contact elements are further included, forming sliding contacts between a slideway of the slipring and the feed line, the two sliding contacts being connected in parallel with one another and electrically conductively connected together via at least one portion of the slideway and via at least one portion of the feed line. Finally, the computed tomography device includes a measuring apparatus, configured to acquire a measured value dependent on a resultant inductance between the two sliding contact elements; and at least one processor, configured to determine an operating state of the two sliding contacts based upon the measured value.

20 Claims, 5 Drawing Sheets

COMPUTED TOMOGRAPHY DEVICE AND METHOD FOR DETERMINING AN OPERATING STATE OF SLIDING CONTACTS IN A COMPUTED TOMOGRAPHY DEVICE

PRIORITY STATEMENT

The present application hereby claims priority under 35 U.S.C. § 119 to European patent application number EP 18178537.9 filed Jun. 19, 2018, the entire contents of which are hereby incorporated herein by reference.

FIELD

Embodiments of the invention generally relate to a computed tomography device and to a method for determining an operating state of sliding contacts on a slipring for rotational transmission in a computed tomography device.

BACKGROUND

Sliprings with one or more sliding contacts are conventionally used to transmit rotation in computed tomography devices. The sliding contacts may for example take the form of carbon and/or brushes. Wear, soiling and/or particular loading may result in a defective sliding contact. A defective sliding contact may cause arcing, which may damage the slipring and in particular lead to abandonment of an examination using the computed tomography device. Since sliding contacts wear over the course of operating time, they have to be regularly replaced.

SUMMARY

The inventors note that conventionally, damage to the slideway caused by arcing is prevented by replacing the sliding contacts very prematurely. The inventors have discovered that this leads to unnecessarily high maintenance costs, since sliding contacts which are worn to a still tolerable extent are also replaced in the process.

At least one embodiment of the invention enables improved determination of the operating state of sliding contacts on a slipring for rotational transmission in a computed tomography device.

Further advantageous aspects and embodiments of the invention are taken into consideration by the claims.

At least one embodiment of the invention relates to a computed tomography device, comprising a slipring for rotational transmission, in particular for rotational transmission of electrical energy for supplying an X-ray source, a feed line, wherein the slipring is arranged to be rotatable relative to the feed line, two sliding contact elements, which form sliding contacts between a slideway of the slipring and the feed line and which are connected in parallel with one another such that the two sliding contact elements are electrically conductively connected together by way of at least one portion of the slideway and by way of at least one portion of the feed line, a measuring apparatus, which is configured to acquire a measured value which is dependent on the resultant inductance between the two sliding contact elements, and a determination unit, which is configured to determine an operating state of the sliding contacts on the basis of the measured value.

At least one embodiment of the invention relates to a computed tomography device, comprising:

a slipring for rotational transmission;

a feed line, the slipring being arranged to be rotatable relative to the feed line;

two sliding contact elements, forming sliding contacts between a slideway of the slipring and the feed line, the two sliding contacts being connected in parallel with one another and electrically conductively connected together via at least one portion of the slideway and via at least one portion of the feed line;

a measuring apparatus, configured to acquire a measured value dependent on a resultant inductance between the two sliding contact elements; and at least one processor, configured to determine an operating state of the two sliding contacts based upon the measured value.

At least one embodiment of the invention further relates to a method for determining an operating state of sliding contacts on a slipring for rotational transmission, in particular for rotational transmission of electrical energy for supplying an X-ray source, in a computed tomography device, wherein the method comprises:

acquiring a measured value which is dependent on the resultant inductance between two sliding contact elements which form the sliding contacts between a slideway of the slipring and a feed line and are connected in parallel with one another such that the two sliding contact elements are electrically conductively connected together by way of at least one portion of the slideway and by way of at least one portion of the feed line, wherein the slipring is arranged so as to be rotatable relative to the feed line, and determining the operating state of the sliding contacts on the basis of the measured value.

At least one embodiment of the invention further relates to a method for determining an operating state of sliding contacts on a slipring for rotational transmission in a computed tomography device, the method comprising:

acquiring a measured value, dependent on a resultant inductance between two sliding contact elements, the two sliding contact elements forming the sliding contacts between a slideway of the slipring and a feed line, connected in parallel with one another such that the two sliding contact elements are electrically conductively connected together via at least one portion of the slideway and via at least one portion of the feed line, wherein the slipring is arranged so as to be rotatable relative to the feed line; and determining the operating state of the two sliding contacts based on the measured value acquired.

BRIEF DESCRIPTION OF THE DRAWINGS

The invention is explained below with reference to example embodiments and to the appended figures. The depictions in the figures are schematic, highly simplified and not necessarily true to scale.

In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a computed tomography device, comprising a slipring for rotational transmission, in particular for rotational transmission of electrical energy for supplying an X-ray source, a feed line, wherein the slipring is arranged to be rotatable relative to the feed line, two sliding contact elements, which form sliding contacts between a slideway of the slipring and the feed line and which are connected in parallel with one another such that the two sliding contact elements are electrically conductively connected together by way of at least one portion of the slideway and by way of at least one portion of the feed line, a measuring apparatus, which is configured to acquire a measured value which is dependent on the resultant inductance between the two sliding contact elements, and a determination unit (which may include one or more appropriately programmed processors), which is configured to determine an operating state of the sliding contacts on the basis of the measured value.

Because a plurality of sliding contact elements are provided which are connected together in parallel, interruption of one of the sliding contacts does not automatically lead to an increase in voltage at the sliding contact element. It is therefore not straightforwardly possible to monitor the operating state of sliding contacts on the basis of a measurement of the voltage drop across the sliding contact elements.

The feed line may in particular be fed with electrical energy, for example in the form of at least one high frequency pulsed current, by an inverter and/or by a DC link. It is therefore not straightforwardly possible to monitor the operating state of sliding contacts on the basis of a measurement of the current distribution across the sliding contact elements. In contrast, in the case of a motor or generator in which very largely sinusoidal current or direct current flows, the operating state of sliding contacts may be monitored on the basis of a measurement of the current distribution across the sliding contact elements. In particular, the resistance of a sliding contact may thus be determined.

One embodiment provides that the determination unit (which may include at one or more appropriately programmed processors) is configured to compare the measured value with a reference value and to determine the operating state of the sliding contacts on the basis of a result of the comparison.

One embodiment provides for the computed tomography device further to include a time series provision unit, which is configured to provide a time series of the measured value and/or of a parameter which may be determined on the basis of the measured value, wherein the determination unit is configured to perform pattern recognition, in particular automatic pattern recognition, on the basis of the time series and to determine the operating state of the sliding contacts on the basis of a result of the pattern recognition. To this end, the determination unit may include one or more appropriately programmed processors.

One embodiment provides for the pattern recognition to be carried out on the basis of a trained machine learning algorithm.

A measured value which is dependent on the resultant inductance between the two sliding contact elements may be acquired, in particular continuously acquired, via the measuring apparatus. The measured value may for example be a value for the resultant inductance or a value for a resonant frequency of an oscillator circuit, which includes the inductance of the at least one portion of the slideway and the inductance of the at least one portion of the feed line. Any known method may be used to measure the resultant inductance.

The measured value may be compared, in particular continuously, with a reference value by way of the determination unit. The reference value may for example be a threshold value, the deviation of which from a standard value is just still tolerable. If the deviation of the resultant inductance from the standard value is greater than the deviation of the reference value from the standard value, a state of the sliding contacts may for example be determined as an operating state of the sliding contacts which requires replacement of at least one of the two sliding contact elements and/or adaptation of the contact pressure of at least one of the two sliding contact elements against the slideway.

The operating state of the sliding contacts may be determined on the basis of a result of the comparison for example by selecting between an operating state of the sliding contact which does not require replacement of at least one of the two sliding contact elements and an operating state of the sliding contacts which does require replacement of at least one of the two sliding contacts. The operating state may in particular for example be displayed via a display apparatus.

In addition to the time series of the measured value and/or of the parameter determined on the basis of the measured value, a further time series may be provided via the time series provision unit which relates to a further parameter which is dependent on the operating state of the computed tomography device and/or which is not dependent on the resultant inductance between the two sliding contact elements. The further parameter may for example be the rotational speed of the rotor of the computed tomography device and/or determined with the assistance of sensors.

Pattern recognition may for example relate to the first time derivative of the measured value, in particular the speed at which the measured value changes over time. Pattern recognition may in particular furthermore be performed on the basis of the further time series. In particular, pattern recognition may relate to a relationship between the measured value and the further parameter in question, for example a relationship between the resultant inductance and the rotational speed.

The machine learning algorithm may for example be trained on the basis of a set of training pairs. The set of training pairs may in particular be provided, wherein each training pair of the set of training pairs includes a training time series and a training operating state which is associated with the training time series.

The training pairs may for example be determined by storing a time profile of the measured value and/or of the parameter during operation of the computed tomography device and in each case determining and storing an operating state of the sliding contacts for one or more instants of the time profile as a training operating state. A portion of the time profile which directly precedes the instant of the training operating state is stored as a training time series. The training operating state is associated with this training time series, such that a training pair is formed. Data, for example the time series and/or the set of training pairs, may be provided by loading the data in particular from a memory system and/or into a processor system.

In particular, for a training operating state relating to defective sliding contacts, a portion of the time profile may be stored which directly precedes the instant at which the defect arose at the sliding contacts and which extends sufficiently far into the past for a pattern indicating an impending occurrence of a defect at the sliding contacts to be identified in the training time series.

One embodiment provides for the measuring apparatus to include a capacitor which forms a parallel resonant circuit with the resultant inductance between the two sliding contact elements, wherein the measured value is a resonant frequency of the parallel resonant circuit.

One embodiment provides for the measuring apparatus to include a coaxial cable and a resonant frequency determination unit which is configured to determine the resonant frequency of the parallel resonant circuit, wherein the two sliding contact elements are connected via the coaxial cable to the resonant frequency determination unit in such a way that the coaxial cable forms at least one part of the capacitor, which, together with the resultant inductance between the two sliding contact elements, forms a parallel resonant circuit.

The capacitor may be formed at least in part by the coaxial cable and/or at least in part by a capacitor. One embodiment provides for the resonant frequency determination unit to be a network analyzer.

One embodiment provides for each of the two sliding contact elements in each case to take the form of a carbon brush. Instead of carbon brushes, other known sliding contact elements may also be used, for example metal brushes, in particular brushes of noble metal wire.

At least one embodiment of the invention further relates to a method for determining an operating state of sliding contacts on a slipring for rotational transmission, in particular for rotational transmission of electrical energy for supplying an X-ray source, in a computed tomography device, wherein the method comprises:

acquiring a measured value which is dependent on the resultant inductance between two sliding contact elements which form the sliding contacts between a slideway of the slipring and a feed line and are connected in parallel with one another such that the two sliding contact elements are electrically conductively connected together by way of at least one portion of the slideway and by way of at least one portion of the feed line, wherein the slipring is arranged so as to be rotatable relative to the feed line, and determining the operating state of the sliding contacts on the basis of the measured value.

One embodiment provides for the measured value to be compared with a reference value, wherein the operating state of the sliding contacts is determined on the basis of a result of the comparison.

One embodiment provides for a time series of the measured value and/or of a parameter determined on the basis of the measured value to be provided, wherein pattern recognition, in particular automatic pattern recognition, is performed on the basis of the time series, and wherein the operating state of the sliding contacts is determined on the basis of the result of the pattern recognition.

One embodiment provides for the pattern recognition to be carried out on the basis of a trained machine learning algorithm.

One embodiment provides for a parallel resonant circuit to be formed from a capacitor and the resultant inductance between the two sliding contact elements, wherein the measured value is a resonant frequency of the parallel resonant circuit.

One embodiment provides that, as a function of the operating state of the sliding contacts, at least one of the two sliding contact elements is replaced and/or a signal is output which indicates that replacement of at least one of the two sliding contact element is necessary. This signal may for example be output in a remote service center which is located in particular outside the hospital in which the computed tomography device is being operated.

One embodiment provides that, as a function of the operating state of the sliding contacts, a contact pressure of at least one of the two sliding contact elements against the slideway is modified, in particular increased.

One embodiment provides for the measured value to be acquired while electrical energy for supplying an X-ray source is transmitted from the feed line to the slideway via the two sliding contact elements.

One embodiment provides for the electrical energy for supplying the X-ray source to be transmitted in the form of at least one high frequency pulsed current. The electrical energy may be converted in the X-ray source at least in part into X-radiation.

Determination of the operating state of the sliding contacts is thus largely independent of the instantaneous voltage and current profile at the sliding contact elements and largely independent of the position of the sliding contact along the slideway, in particular largely independent of whether a zero crossover of the current or of the voltage with which the electrical energy is transmitted is present in the region of the sliding contact. Determination of the operating status of the sliding contacts thus proceeds largely unimpaired by interference arising during transmission of the electrical energy for operation of an X-ray tube. Such interference may for example be harmonics from inverters.

Furthermore, the operating state of sliding contacts provided for rotational transmission of a protective conductor may be determined in this way. In particular, it is not necessary for this purpose to feed a test current into the protective conductor.

The operating state of the sliding contacts may therefore in particular also be determined during an acquisition process, in which X-radiation is generated via the X-ray tube and acquired via an X-ray detector after interaction with a region of the patient to be imaged.

As a function of the operating state of the sliding contacts, at least one of the two sliding contact elements may be replaced and/or an instant or a time interval determined for replacement of at least one of the two sliding contact elements. Because the operating state of the sliding contact elements may be continuously monitored, the service life of the sliding contact elements may be largely fully utilized and possible damage to the slideway by defective sliding contacts may be largely avoided. In this way, maintenance costs may be reduced, abandonment of examinations caused by defective sliding contacts may be avoided and downtimes for the computed tomography device may be better planned.

A machine learning algorithm is understood in the context of this application in particular to mean an algorithm which is configured for machine learning. A machine learning algorithm may for example be implemented using decision trees, mathematical functions and/or general programming languages. The machine learning algorithm may for example be configured for monitored learning and/or for unmonitored learning. The machine learning algorithm may for example be configured for deep learning and/or reinforcement learning and/or for marginal space learning. In the case of monitored learning in particular, it is possible to use a function class which is based for example on decision trees, a random forest, a logistic regression, a support vector machine, an artificial neural network, a kernel method, Bayes classifiers or the like or combinations thereof. Possible implementations of the machine learning algorithm may for example use artificial intelligence. Calculations, in particular during training of a machine learning algorithm, may for example be performed using a processor system. The processor system may for example include one or more processors, in particular graphics processors.

In the context of embodiments of the invention, features which are described in relation to different embodiments of the invention and/or different categories of claim (method, use, apparatus, system, arrangement etc.) may be combined to yield further embodiments of the invention. For example, a claim relating to an apparatus may also be further developed with features which are described or claimed in connection with a method and vice versa. Functional features of a method may in this case be embodied by appropriately configured physical components. In addition to the embodiments of the invention explicitly described in this application, many and varied further embodiments of the invention are conceivable, at which a person skilled in the art may arrive without going beyond the scope of the invention insofar as it is specified by the claims.

Use of the indefinite article "a" or "an" does not rule out the possibility of the feature in question also being present in multiple instances. Use of the numeral "two" does not rule out the possibility of the feature in question also being present more than twice. Use of the term "include" does not rule out the possibility of the terms linked by the term "include" being identical. For example, the medical imaging apparatus includes the medical imaging apparatus. Use of the term "unit" does not rule out the possibility of the object to which the term "unit" relates including a plurality of components which are spatially separated from one another.

The expression "on the basis of" may be understood, in the context of the present application, in particular to mean "using". In particular, wording according to which a first feature is generated (or: determined, established etc.) on the basis of a second feature does not rule out the possibility of the first feature being generated (or: determined, established etc.) on the basis of a third feature.

Figure 1:
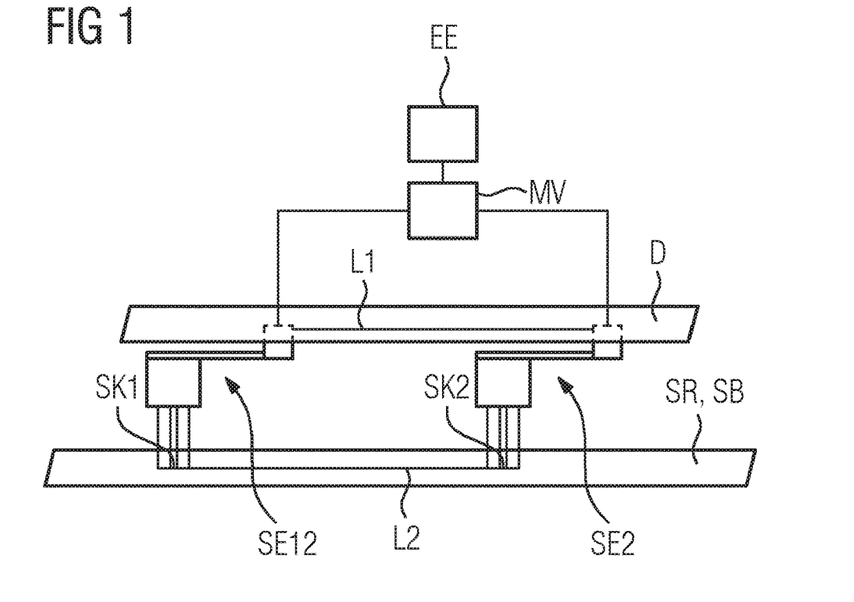
FIG. 1 shows an example embodiment with a slipring, a feed line and two sliding contact elements.

FIG. 1 shows the slipring SR with the slideway SB, the feed line D, the sliding contact elements SE1 and SE2, the sliding contacts SK1 and SK2, the measuring apparatus MV and the determination unit EE. The slipring SR includes the slideway SB and is arranged so as to be rotatable relative to the feed line D. The two sliding contact elements SE1 and SE2 are arranged on the feed line D. Each of the two sliding contact elements SE1 and SE2 in each case takes the form of a brush, for example a carbon brush.

Each of the two sliding contact elements SE1 and SE2 is connected with the feed line D via a spring element and in each case a contact pressure adjusting apparatus which is configured to adjust the contact pressure of the brush against the slideway SB. One end of the spring element is firmly connected with the feed line D. The other end of the spring element is firmly connected with the brush. The spring element may for example include a resilient metal strip, which is clamped at one end in the region of the feed line D. The contact pressure adjusting apparatus may for example include a thread and/or be configured to modify the distance between the brush and the feed line D. By increasing the distance between the brush and the feed line D, it is possible to increase the contact pressure of the brush against the slideway SB. In the case of a brush which has been worn away by wear, it is possible in this way to reestablish sliding contact function.

The two sliding contact elements SE1 and SE2 are connected together in parallel in such a way that the two sliding contact elements SE1 and SE2 are electrically conductively connected together by way of the portion L2 of the slideway SB and by way of the portion L1 of the feed line D. The two sliding contact elements SE1 and SE2 are arranged on the same printed conductor portion of the feed line D. The slideway SB is connected electrically conductively with the feed line D both by way of the sliding contact element SE1 and by way of the sliding contact element SE2. Sliding contact element SE1 is a first carbon brush. Sliding contact element SE2 is a second carbon brush.

One or more further sliding contact elements, not shown in FIG. 1, may also be provided which in each case form a sliding contact between the slideway and the feed line. Instead of a printed conductor, stranded wire may for example be used for the feed line D, in order to connect the two sliding contact elements SE1 and SE2 together electrically conductively. In particular, a plurality of printed conductor portions may be provided. In particular, in each case one printed conductor portion and in each case one slideway of the slipring SR may be provided for each phase of a multiphase electrical energy transmission.

The resultant inductance between the two sliding contact elements SE1 and SE2 depends in particular on the inductance of the portion L1 of the feed line D, on the inductance of the portion L2 of the slideway SB and on the operating state of the sliding contacts SK1 and SK2. If the sliding contacts SK1 and SK2 are optimally configured, the resultant inductance substantially corresponds to parallel connection of the inductance of the portion L1 and the inductance of the portion L2. If at least one of the sliding contacts SK1 and SK2 is interrupted, the resultant inductance substantially corresponds to the inductance of portion L1.

Figure 2:
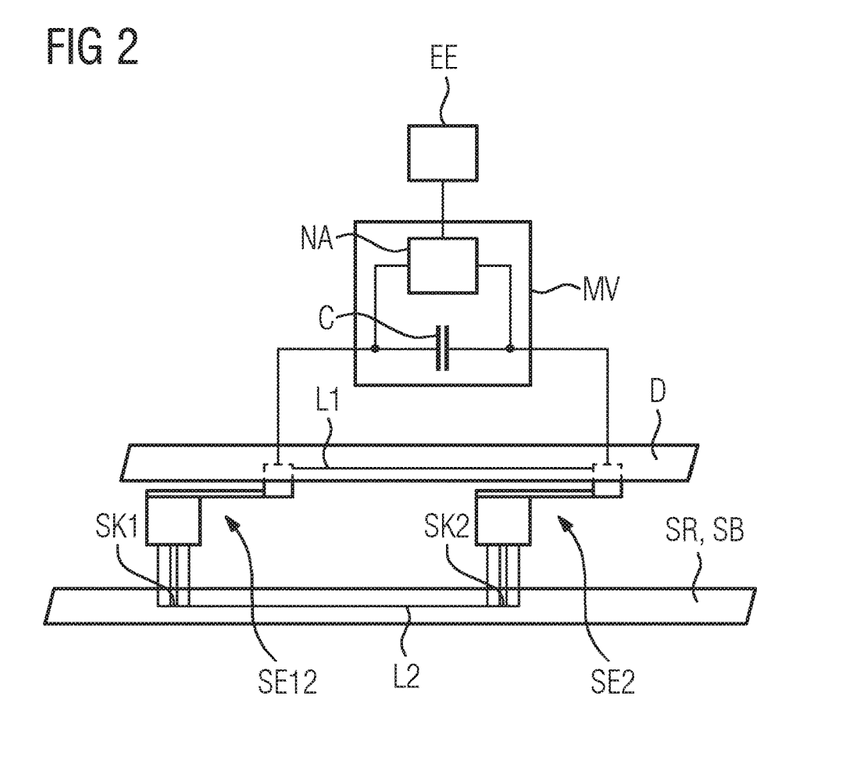
FIG. 2 shows an example embodiment with a slipring, a feed line and two sliding contact elements together with a capacitor.

FIG. 2 shows the slipring SR with slideway SB, the feed line D, the sliding contact element SE1 and SE2, the sliding contacts SK1 and SK2, the measuring apparatus MV and the determination unit EE. The measuring apparatus MV includes a capacitor C which forms a parallel resonant circuit with the resultant inductance between the two sliding contact elements SE1 and SE2. The two sliding contact elements SE1 and SE2 are connected together via the capacitor C and the capacitor C is connected in parallel to the portion L1 of the feed line. The measuring apparatus MV further comprises a vector network analyzer NA as the resonant frequency determination unit with which the resonant frequency of the parallel resonant circuit may be determined.

Figure 3:
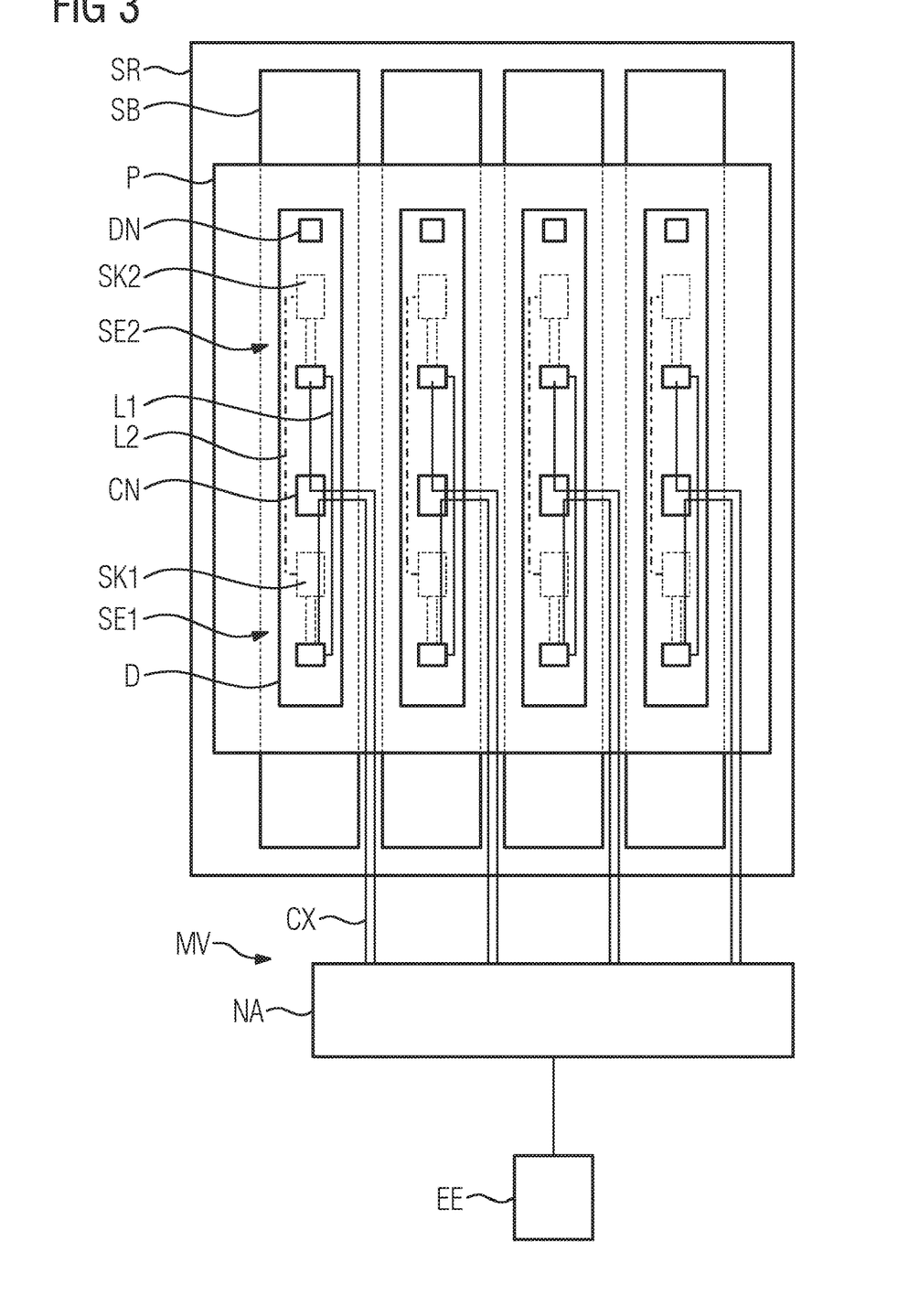
FIG. 3 shows an example embodiment with a slipring, including a plurality of a slideways, and a plurality of feed lines.

FIG. 3 shows the slipring SR, which includes a plurality of slideways, and the printed circuit board P, which includes a plurality of feed lines in the form of printed conductors. The slipring SR is arranged so as to be rotatable relative to the printed circuit board P. Three feed lines are provided for the three phases of a three-phase electrical energy transmission. A fourth feed line is provided together with the corresponding slideway for rotational transmission of the protective conductor. At each of the four feed lines, two sliding contact elements are arranged which are each connected with a resonant frequency determination unit by way of one of four coaxial cables associated with the respective feed line.

For each of the four feed lines in each case a resonant frequency is acquired which is dependent on the resultant inductance between the two sliding contact elements of the feed line. The resonant frequency determination unit may in particular be configured to determine the four resonant frequencies at the same time. To this end, the resonant frequency determination unit may for example include a four-channel network analyzer NA or four single-channel network analyzers. Alternatively, the resonant frequency determination unit is configured to switch over between the four coaxial cables such that the four resonant frequencies are determined repeatedly and successively over time. A single-channel network analyzer would thus be sufficient to determine all four resonant frequencies.

Figure 4:
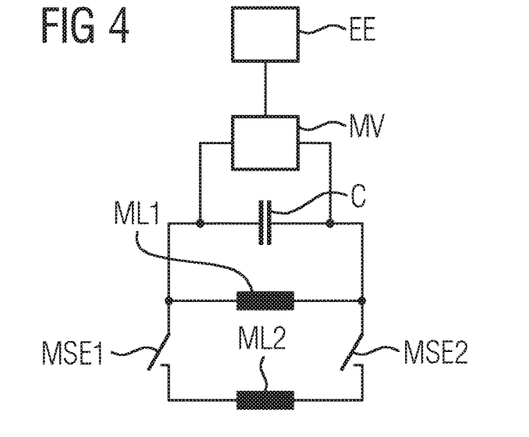
FIG. 4 shows a circuit diagram with a parallel resonant circuit.

FIG. 4 shows a circuit diagram with a parallel resonant circuit, the measuring apparatus MV and the determination unit EE.

The parallel resonant circuit includes the capacitor C and the inductor ML1. If both switches MSE1 and MSE2 are closed, the parallel resonant circuit further includes the inductor ML2, such that the resultant inductance of the parallel resonant circuit corresponds to a parallel connection of inductors ML1 and ML2. Inductor ML1 substantially corresponds to the inductance of portion L1 of the feed line D. Inductor ML2 substantially corresponds to the inductance of portion L2 of the slideway SB.

Switch MSE1 corresponds to sliding contact element SE1. Switch MSE2 corresponds to sliding contact element SE2. A closed switch corresponds to an intact sliding contact between slideway SB and feed line D. An open switch corresponds to a defective, in particular interrupted, sliding contact between slideway SB and feed line D.

Figure 5:
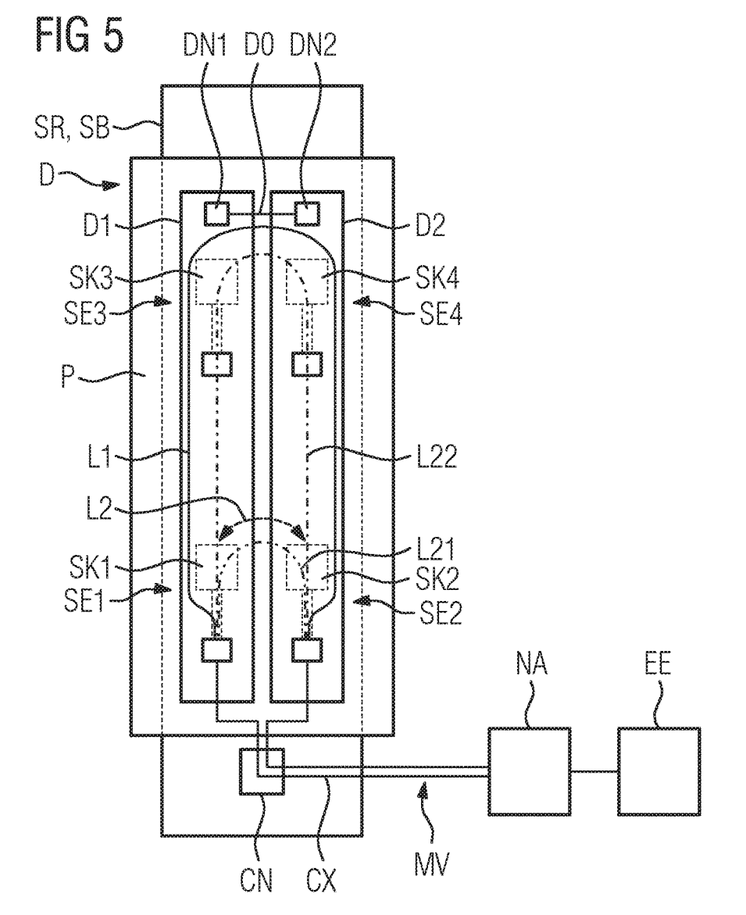
FIG. 5 shows an example embodiment with a feed line which has two printed conductor portions.

In the example shown in FIG. 5, the feed line D includes a first printed conductor portion D1, a second printed conductor portion D2, which is arranged parallel to the first printed conductor portion D1, and a connection line D0, which electrically conductively connects the second printed conductor portion D2 with the first printed conductor portion D1. Connection line D0 may for example be a stranded wire. Connection line D0 is connected with terminal DN1 of the first printed conductor portion D1 and terminal DN2 of the second printed conductor portion D2.

In this way, a portion L1 of the feed line may be produced which has a relatively large length and thus a relatively high inductance. A parallel resonant circuit may thus be formed, the resonant frequency of which depends even more sensitively on the inductance of the portion L2 of the slideway. The inductance of portion L2 of the slideway SB results from the inductances of a plurality of paths, which connect the two sliding contact elements SE1 and SE2 together in a more electrically conductive manner. In particular, the two sliding contact elements SE1 and SE2 are electrically conductively connected together by way of the paths L21 and L22.

The two sliding contact elements SE1 and SE3 are arranged on the first printed conductor portion D1 of feed line D. The two sliding contact elements SE2 and SE4 are arranged on the second printed conductor portion D1 of feed line D. The sliding contact element SE1 forms the sliding contact SK1 between the slideway SB and the first conductor portion D1 of the feed line D. The sliding contact element SE3 forms the sliding contact SK3 between the slideway SB and the first conductor portion D1 of the feed line D. The sliding contact element SE2 forms the sliding contact SK2 between the slideway SB and the second conductor portion D2 of the feed line D. The sliding contact element SE4 forms the sliding contact SK4 between the slideway SB and the second conductor portion D2 of the feed line D.

The measuring apparatus MV includes a vector network analyzer NA as resonant frequency-determination unit. The vector network analyzer NA is connected with the two sliding contact elements SE1 and SE2 by way of the coaxial cable CX and the plug connector CN, for example in the form of an SMA connection. The capacitor of the coaxial cable CX forms a parallel resonant circuit with the resultant inductance between the two sliding contact elements SE1 and SE2.

Figure 6:
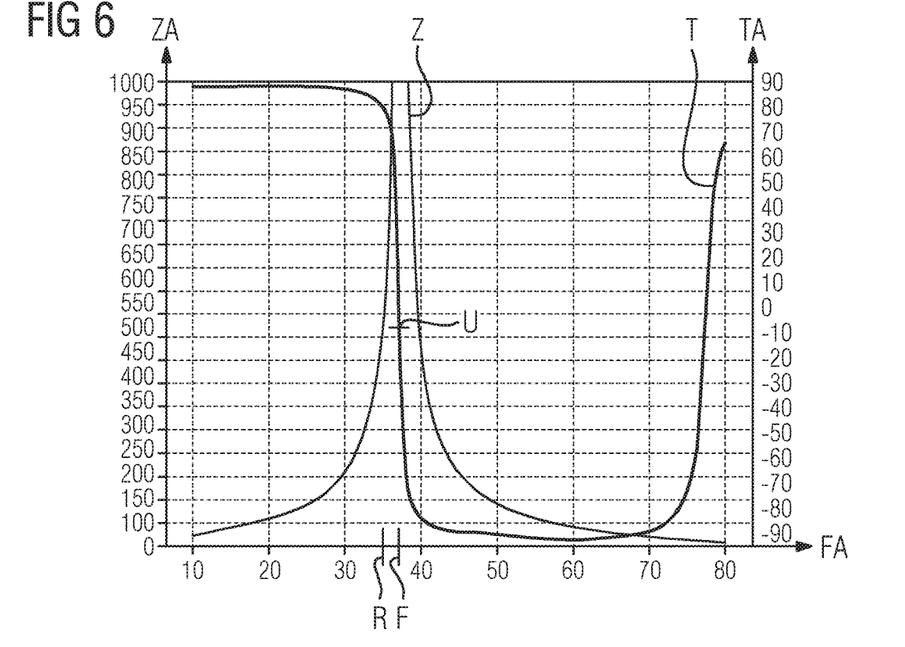
FIG. 6 shows a diagram relating to the impedance of the parallel resonant circuit.

FIG. 6 shows a diagram in which the magnitude Z and the phase angle T of the impedance of the parallel resonant circuit have been plotted as a function of frequency, wherein the sliding contact elements SE1 and SE2 rest with a marginally low contact pressure against the slideway SB and form the sliding contacts SK1 and SK2.

On the axis ZA, values are plotted in ohms for the magnitude Z of the impedance of the parallel resonant circuit. On the axis TA, values are plotted in degrees for the phase angle T of the impedance of the parallel resonant circuit. On the axis FA, values are plotted in megahertz for frequency. The marker U is located at the resonant frequency F of approximately 37 megahertz, which is greater than the reference value R of approximately 35 megahertz.

Figure 7:
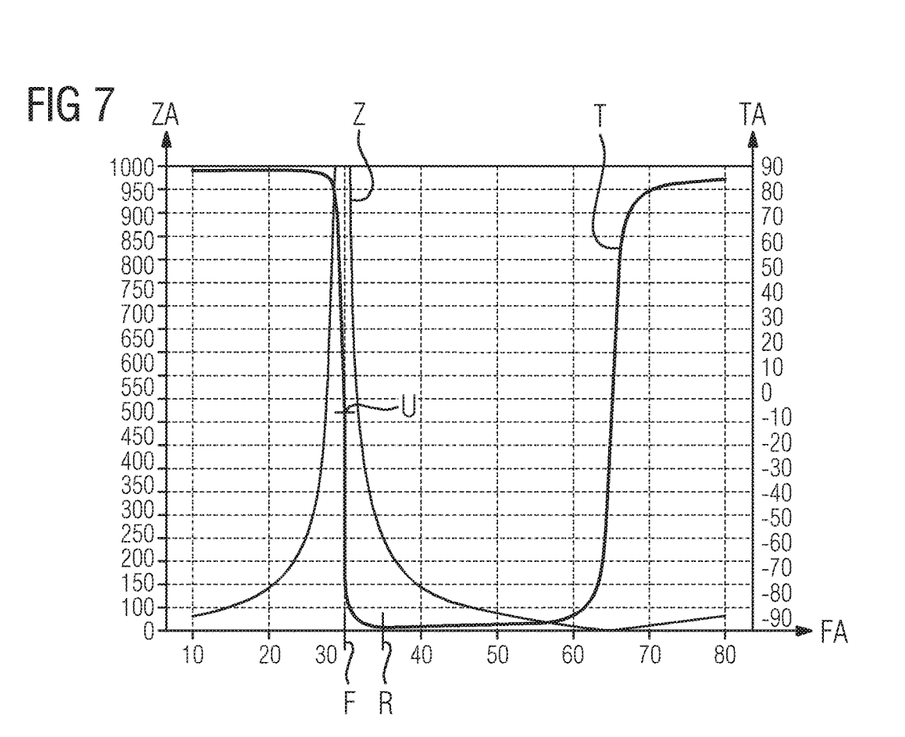
FIG. 7 shows a diagram relating to the impedance of the parallel resonant circuit, wherein a sliding contact has been interrupted.

FIG. 7 shows a diagram where one of the sliding contact elements SE1 and SE2 has been insulated from the slideway SB using a thin film, such that the corresponding sliding contact is interrupted. The marker U is located at the resonant frequency F of approximately 30 megahertz, which is less than the reference value R of approximately 35 megahertz.

Figure 8:
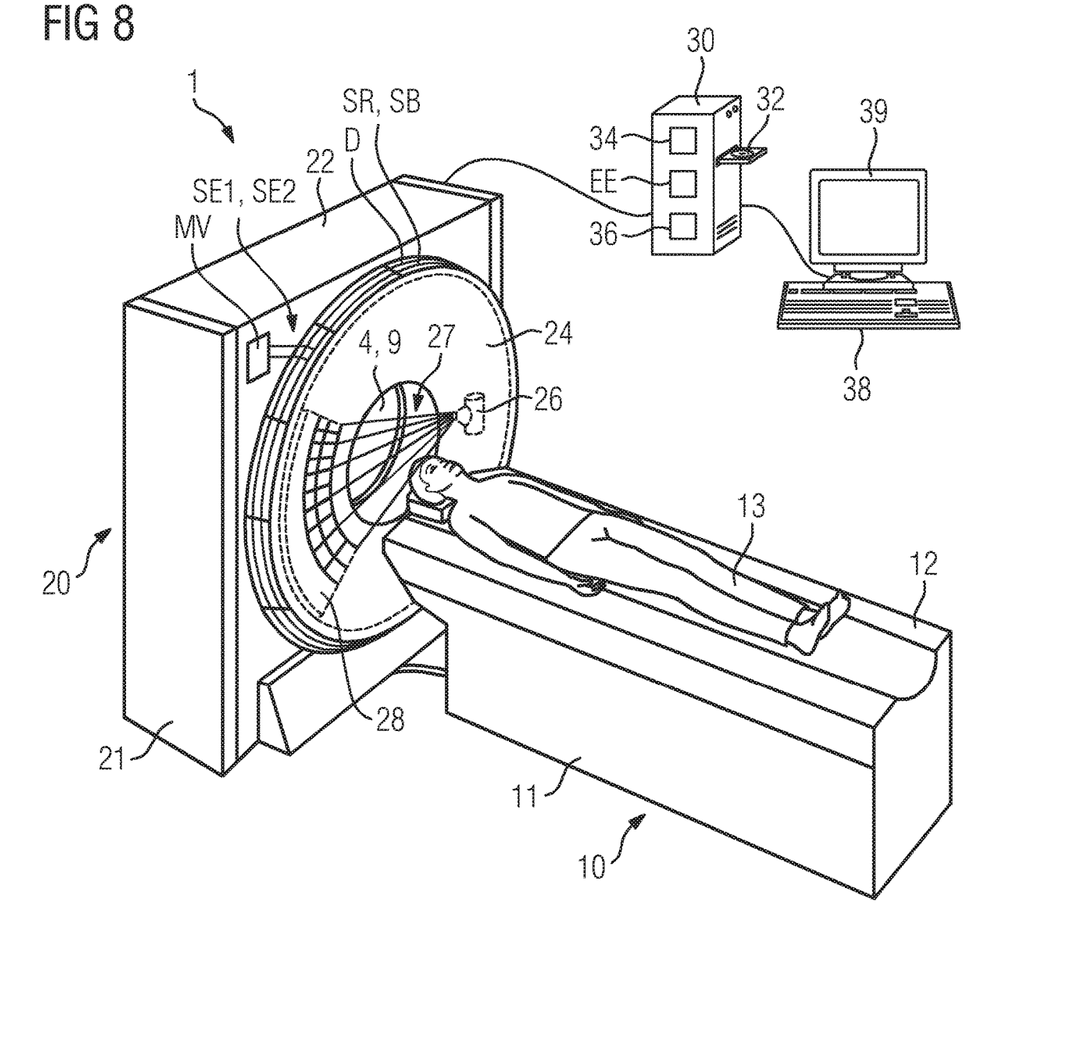
FIG. 8 shows a computed tomography device and FIG. 9 is a flow chart of a method for determining an operating state of sliding contacts.

FIG. 8 shows the computed tomography device 1, which includes the gantry 20, the tunnel-shaped opening 9, the patient positioning apparatus 10 and the control apparatus 30. The gantry 20 includes the mounting frame 21, the tilting frame 22 and the rotor 24. The tilting frame 22 is arranged on the mounting frame 21 by way of a tilting bearing apparatus so as to be tiltable about a tilt axis relative to the mounting frame 21. The rotor 24 is arranged on the tilting frame 22 by way of a pivot bearing apparatus so as to be rotatable about an axis of rotation relative to the tilting frame 22. The tilt axis is horizontal and perpendicular to the axis of rotation.

The computed tomography device 1 includes the slipring SR with the slideway SB, the feed line D, the two sliding contact elements SE1 and SE2, which form the sliding contacts SK1 and SK2 between the slideway SB of the slipring SR and the feed line D, the measuring apparatus MV and the determination unit EE. The feed line D is arranged on the tilting frame 22 stationarily relative to the tilting frame 22. The slipring SR is arranged on the rotor 24 stationarily relative to the rotor 24. The slipring SR is thus arranged to be rotatable relative to the feed line D, in particular rotatable about the axis of rotation of the rotor 24.

The patient 13 may be introduced into the tunnel-shaped opening 9. The acquisition region 4 is located in the tunnel-shaped opening 9. A region of the patient 13 to be imaged may be positioned in the acquisition region 4 in such a way that the radiation 27 from the radiation source 26 may reach the region to be imaged and, after interaction with the region to be imaged, may reach the radiation detector 28.

The patient positioning apparatus 10 includes the positioning base 11 and the positioning bed 12 for positioning the patient 13. The positioning bed 12 is arranged on the positioning base 11 so as to be movable relative to the positioning base 11 in such a way that the positioning bed 12 may be introduced into the acquisition region 4 in a longitudinal direction of the positioning bed 12.

The computed tomography device 1 is configured for the acquisition of acquisition data on the basis of electromagnetic radiation 27 and includes an acquisition unit. The acquisition unit is a projection data acquisition unit with the radiation source 26, e.g. an X-ray source, in particular an X-ray tube, and the detector 28, e.g. an X-ray detector, in particular an energy-resolving X-ray detector.

The radiation source 26 is arranged on the rotor 24 and configured for emission of radiation 27, e.g. X-radiation, with radiation quanta 27. The detector 28 is arranged on the rotor 24 and configured for detection of the radiation quanta 27. The radiation quanta 27 may travel from the radiation source 26 to the region of the patient 13 to be imaged and impinge on the detector 28 after interaction with the region to be imaged. In this way, the acquisition unit can acquire acquisition data of the region to be imaged in the form of projection data.

The control apparatus 30 is configured to receive the acquisition data acquired by the acquisition unit. The control apparatus 30 is configured to control the computed tomography device 1.

The control apparatus 30 includes the determination unit EE, the computer-readable medium 32 and the processor system 36. The control apparatus 30, in particular the determination unit EE, is formed by a data processing system which includes a computer. The control apparatus 30 includes the image reconstruction apparatus 34. Using the image reconstruction apparatus 34, it is possible to reconstruct a medical image data set on the basis of the acquisition data.

The medical imaging apparatus 1 includes an input apparatus 38 and an output apparatus 39, each of which are connected to the control apparatus 30. The input apparatus 38 is configured for inputting control information, e.g. image reconstruction parameters, examination parameters or the like. The output apparatus 39 is configured in particular to output control information, images and/or acoustic signals. The operating state of the sliding contacts SK1 and SK2 may in particular be displayed via the output apparatus 39.

Figure 9:
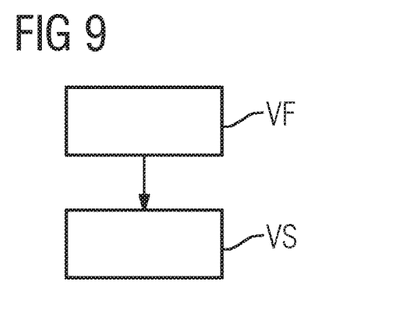

FIG. 9 shows a sequence diagram for a method for determining the operating state of the sliding contacts SK1 and SK2 at the slipring SR for rotational transmission in the computed tomography device 1, wherein the method comprises the following steps:

acquiring VF a measured value F which is dependent on the resultant inductance between two sliding contact elements SE1, SE2, which form the sliding contacts SK1, SK2 between a slideway SB of the slipring SR and a feed line D and which are connected in parallel with one another in such a way that the two sliding contact elements SE1 and SE2 are electrically conductively connected together by way of at least one portion L2 of the slideway SB and by way of at least one portion L1 of the feed line D, wherein the slipring SR is arranged so as to be rotatable relative to the feed line D, and determining VS the operating state of the sliding contacts SK1 and SK2 on the basis of the measured value F.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography device, comprising:
   a slipring for rotational transmission;
   a feed line, the slipring being arranged to be rotatable relative to the feed line;
   two sliding contact elements, forming two sliding contacts between a slideway of the slipring and the feed line, the two sliding contacts being connected in parallel with one another and electrically conductively connected together via at least one portion of the slideway and via at least one portion of the feed line;
   a measuring apparatus, configured to acquire a measured value dependent on a resultant inductance between the two sliding contact elements; and
   at least one processor, configured to determine an operating state of the two sliding contacts based upon the measured value.

2. The computed tomography device of claim 1, wherein the at least one processor is configured to compare the measured value with a reference value and determine a result and wherein the at least one processor is further configured to determine an operating state of the two sliding contacts based upon the result.

3. The computed tomography device of claim 2,
   wherein the measuring apparatus includes a capacitor, forming a parallel resonant circuit with the resultant inductance between the two sliding contact elements, and
   wherein the measured value is a resonant frequency of the parallel resonant circuit.

4. The computed tomography device of claim 3,
   wherein the measuring apparatus includes a coaxial cable and a resonant frequency determination device configured to determine the resonant frequency of the parallel resonant circuit, and
   wherein the two sliding contact elements are connected via the coaxial cable to the resonant frequency determination device, the coaxial cable forming at least one part of the capacitor and, together with the resultant inductance between the two sliding contact elements, forming a parallel resonant circuit.

5. The computed tomography device of claim 4,
   wherein the resonant frequency determination device is a network analyzer.

6. The computed tomography device of claim 1,
   wherein the measuring apparatus includes a capacitor, forming a parallel resonant circuit with the resultant inductance between the two sliding contact elements, and
   wherein the measured value is a resonant frequency of the parallel resonant circuit.

7. The computed tomography device of claim 6,
   wherein the measuring apparatus includes a coaxial cable and a resonant frequency determination device configured to determine the resonant frequency of the parallel resonant circuit, and
   wherein the two sliding contact elements are connected via the coaxial cable to the resonant frequency determination device, the coaxial cable forming at least one part of the capacitor and, together with the resultant inductance between the two sliding contact elements, forming a parallel resonant circuit.

8. The computed tomography device of claim 7,
   wherein the resonant frequency determination device is a network analyzer.

9. The computed tomography device of claim 1,
   wherein each of the two sliding contact elements takes a form of a carbon brush.

10. A method for determining an operating state of sliding contacts on a slipring for rotational transmission in a computed tomography device, the method comprising:
    acquiring a measured value, dependent on a resultant inductance between two sliding contact elements, the two sliding contact elements forming two sliding contacts between a slideway of the slipring and a feed line, connected in parallel with one another such that the two sliding contact elements are electrically conductively connected together via at least one portion of the slideway and via at least one portion of the feed line, wherein the slipring is arranged so as to be rotatable relative to the feed line; and
    determining the operating state of the two sliding contacts based on the measured value acquired.

11. The method of claim 10, further comprising:
    comparing the measured value is compared with a reference value, wherein the operating state of the sliding contacts is determined, during the determining, based upon a result of the comparing.

12. The method of claim 11, further comprising:
    determining a time series based upon the measured value;
    performing pattern recognition based on the time series determined, and
    wherein the operating state of the sliding contacts is determined, during the determining, based upon a result of the performing of the pattern recognition.

13. The method as claimed in claim 12,
    wherein the pattern recognition performed, during the performing, based upon a trained machine learning algorithm.

14. The method of claim 10, further comprising:
    determining a time series based upon the measured value;
    performing pattern recognition based on the time series determined, and
    wherein the operating state of the sliding contacts is determined, during the determining, based upon a result of the performing of the pattern recognition.

15. The method as claimed in claim 14,
wherein the pattern recognition performed, during the performing, based upon a trained machine learning algorithm.

16. The method of claim 10, wherein a parallel resonant circuit is formed from a capacitor and a resultant inductance between the two sliding contact elements, and wherein the measured value is a resonant frequency of the parallel resonant circuit.

17. The method of claim 10, wherein, as a function of the operating state of the two sliding contacts determined, at least one of the two sliding contact elements is replaced.

18. The method of claim 10, wherein, as a function of the operating state of the sliding contacts determined, a contact pressure of at least one of the two sliding contact elements against the slideway is modified.

19. The method of claim 10, wherein the measured value is acquired while electrical energy for supplying an X-ray source is transmitted from the feed line to the slideway, via the two sliding contact elements.

20. The method of claim 19, wherein the electrical energy for supplying the X-ray source is transmitted in a form of at least one high frequency pulsed current.

\* \* \* \* \*